(12) United States Patent
Yamada et al.

(10) Patent No.: US 10,568,495 B2
(45) Date of Patent: Feb. 25, 2020

(54) SCANNING ENDOSCOPE SYSTEM

(71) Applicant: OLYMPUS CORPORATION, Tokyo (JP)

(72) Inventors: Masashi Yamada, Tokyo (JP);
Atsuyoshi Shimamoto, Tokyo (JP);
Mitsuru Namiki, Saitama (JP);
Keiichiro Nakajima, Tokyo (JP);
Takamitsu Sakamoto, Tokyo (JP);
Mikihiko Terashima, Tokyo (JP); Yoko Okabe, Tokyo (JP); Yu Kondo, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 104 days.

(21) Appl. No.: 15/846,537

(22) Filed: Dec. 19, 2017

(65) Prior Publication Data

US 2018/0116492 A1    May 3, 2018

Related U.S. Application Data

(63) Continuation of application No. PCT/JP2016/068013, filed on Jun. 16, 2016.

(30) Foreign Application Priority Data

Mar. 4, 2016   (JP) ................. 2016-042461

(51) Int. Cl.
*A61B 1/04*       (2006.01)
*A61B 1/07*       (2006.01)
(Continued)

(52) U.S. Cl.
CPC ............ *A61B 1/04* (2013.01); *A61B 1/00009* (2013.01); *A61B 1/00045* (2013.01);
(Continued)

(58) Field of Classification Search
CPC ... A61B 1/00172; A61B 1/07; A61B 1/00096; A61B 1/0638; A61B 1/00165;
(Continued)

(56) References Cited

U.S. PATENT DOCUMENTS

| 4,898,175 A | 2/1990 | Noguchi |
| 6,294,775 B1 | 9/2001 | Seibel et al. |

(Continued)

FOREIGN PATENT DOCUMENTS

| EP | 2351508 A1 | 8/2011 |
| EP | 2946717 A1 | 11/2015 |

(Continued)

OTHER PUBLICATIONS

International Search Report dated Sep. 8, 2015 issued in PCT/JP2015/068195.

(Continued)

*Primary Examiner* — Tracy Y. Li
*Assistant Examiner* — Samuel D Fereja
(74) *Attorney, Agent, or Firm* — Scully, Scott, Murphy & Presser, P.C.

(57) ABSTRACT

Provided is a scanning endoscope system including: an illumination-light emitting portion that is inserted into a body of a patient and that emits illumination light emitted from a light-source portion toward an imaging subject in the body in a spot-like manner; a light scanner that scans the illumination light on the imaging subject; and a light detector that is disposed at a body surface of the patient, and that detects reflected light coming from the scanning position in the imaging subject, at which the illumination light is scanned by the light scanner.

14 Claims, 15 Drawing Sheets

(51) Int. Cl.
| | |
|---|---|
| *H04N 5/235* | (2006.01) |
| *G02B 23/24* | (2006.01) |
| *G02B 26/10* | (2006.01) |
| *A61B 1/00* | (2006.01) |
| *A61B 1/06* | (2006.01) |
| *H04N 9/04* | (2006.01) |
| *A61B 1/317* | (2006.01) |
| *H04N 5/225* | (2006.01) |
| *H04N 5/33* | (2006.01) |

(52) U.S. Cl.
CPC .......... *A61B 1/00172* (2013.01); *A61B 1/042* (2013.01); *A61B 1/0638* (2013.01); *A61B 1/0646* (2013.01); *A61B 1/07* (2013.01); *A61B 1/317* (2013.01); *G02B 23/2407* (2013.01); *G02B 23/2423* (2013.01); *G02B 23/2453* (2013.01); *G02B 23/2469* (2013.01); *G02B 23/2476* (2013.01); *G02B 26/103* (2013.01); *H04N 5/2256* (2013.01); *H04N 5/2354* (2013.01); *H04N 5/332* (2013.01); *H04N 9/04557* (2018.08); *H04N 2005/2255* (2013.01)

(58) Field of Classification Search
CPC ..... A61B 5/0066; A61B 5/0062; A61B 1/043; A61B 1/00; A61B 1/00009; A61B 5/0071; A61B 5/0084; A61B 1/05; A61B 1/0008; A61B 1/00006; A61B 1/04; A61B 1/045; A61B 1/0646; A61B 5/0068; A61B 1/0661; A61B 5/6852; A61B 1/00177; A61B 1/0615; A61B 1/0669; A61B 1/00167; A61B 1/00183; A61B 1/00188; A61B 1/042; A61B 1/063; A61B 1/0005; A61B 1/00186; A61B 1/00193; A61B 1/06; A61B 5/0073; A61B 5/0086; A61B 18/24; A61B 1/00057; A61B 1/00105; A61B 1/00179; A61B 1/0051; A61B 1/0623; A61B 1/0684; A61B 2562/0242; A61B 5/0064; A61B 5/0075; A61B 5/1076; A61B 1/00045; A61B 1/00059; A61B 1/00098; A61B 1/0011; A61B 1/0676; A61B 2017/00057; A61B 3/102; A61B 3/12; A61B 5/489; A61B 17/068; A61B 17/29; A61B 1/00036; A61B 1/00087; A61B 1/00103; A61B 1/0017; A61B 1/005; A61B 1/0125; A61B 1/051; A61B 1/0607; A61B 1/0653; A61B 1/313; A61B 1/3132; A61B 2017/00137; A61B 2017/00278; A61B 2018/00982; A61B 2090/306; A61B 2090/3614; A61B 2562/0238; A61B 2562/028; A61B 3/0008; A61B 3/0058; A61B 3/1025; A61B 3/14; A61B 5/0059; A61B 5/0088; A61B 5/0095; A61B 5/02007; A61B 5/065; A61B 5/067; A61B 5/08; A61B 5/0873; A61B 5/14546; A61B 5/418; A61B 5/4255; A61B 5/441; A61B 5/444; A61B 5/445; A61B 5/7239; A61B 5/7425; A61B 8/12; A61B 8/4461; A61B 90/20; G02B 26/103; G02B 23/26; G02B 23/2469; G02B 23/2423; G02B 26/10; G02B 23/243; G02B 23/24; G02B 23/2476; G02B 23/2484
See application file for complete search history.

(56) References Cited

U.S. PATENT DOCUMENTS

| | | | |
|---|---|---|---|
| 2007/0027362 | A1 | 2/2007 | Handa et al. |
| 2007/0244357 | A1* | 10/2007 | Wiklof ................ A61B 1/0008 600/109 |
| 2007/0244365 | A1* | 10/2007 | Wiklof ................ A61B 1/0008 600/173 |
| 2008/0165360 | A1 | 7/2008 | Johnston |
| 2010/0168515 | A1* | 7/2010 | Sugimoto ............ A61B 1/0008 600/109 |
| 2011/0282213 | A1 | 11/2011 | Kawano |
| 2012/0147165 | A1 | 6/2012 | Yoshino et al. |
| 2013/0003131 | A1 | 1/2013 | Johnston |
| 2013/0155215 | A1* | 6/2013 | Shimada ............ A61B 1/00172 348/68 |
| 2015/0141753 | A1* | 5/2015 | Kanamori ........ H01L 27/14627 600/109 |
| 2015/0294466 | A1 | 10/2015 | Johnston |
| 2015/0374219 | A1 | 12/2015 | Yoshino |

FOREIGN PATENT DOCUMENTS

| | | |
|---|---|---|
| JP | S5421678 B2 | 8/1979 |
| JP | S63161936 A | 7/1988 |
| JP | H109294705 A | 11/1997 |
| JP | 2007029454 A | 2/2007 |
| JP | 2010133842 A | 6/2010 |
| JP | 2012125293 A | 7/2012 |
| JP | 2014124381 A | 7/2014 |
| JP | 5608718 B2 | 10/2014 |
| JP | 2015112278 A | 6/2015 |
| WO | 2008085186 A1 | 7/2008 |
| WO | 2010061471 A1 | 6/2010 |
| WO | 2015004961 A1 | 1/2015 |

OTHER PUBLICATIONS

International Search Report dated Sep. 6, 2016 issued in PCT/JP2016/068013.

* cited by examiner

SCANNING ENDOSCOPE SYSTEM

CROSS-REFERENCE TO RELATED APPLICATIONS

This is a continuation of International Application PCT/JP2016/068013, with an international filing date of Jun. 16, 2016, which is hereby incorporated by reference herein in its entirety. This application claims the benefits of Japanese Patent Application No. 2016-042461 and International Application PCT/JP2015/068195, the contents of which are incorporated herein by reference.

TECHNICAL FIELD

The present invention relates to a scanning endoscope system.

BACKGROUND ART

In the related art, there is a known scanning endoscope with which illumination light is scanned on an imaging subject by causing an illumination optical fiber that guides the illumination light to vibrate, and reflected light of the illumination light coming from an imaging subject surface is received by a detection optical fiber, thus forming an image (for example, see Patent Literature 1). In this scanning endoscope, a plurality of detection optical fibers are arranged next to each other along a circumferential direction of a columnar scanning unit, which causes the illumination optical fiber to vibrate, and are secured thereto.

CITATION LIST

Patent Literature

{PTL 1} Publication of U.S. Pat. No. 6,294,775, Specification

SUMMARY OF INVENTION

An aspect of the present invention is a scanning endoscope system including: an illumination-light emitting portion that is inserted into a body of a patient and that emits illumination light emitted from a light-source portion toward an imaging subject in the body in a spot-like manner; a light-scanning portion that scans the illumination light on the imaging subject; and a light-detecting portion that is disposed at a body surface of the patient, and that detects reflected light coming from the scanning position in the imaging subject, at which the illumination light is scanned by the light-scanning portion.

DESCRIPTION OF EMBODIMENT

A scanning endoscope system 1 according to an embodiment of the present invention will be described below with reference to the drawings.

Figure 1:
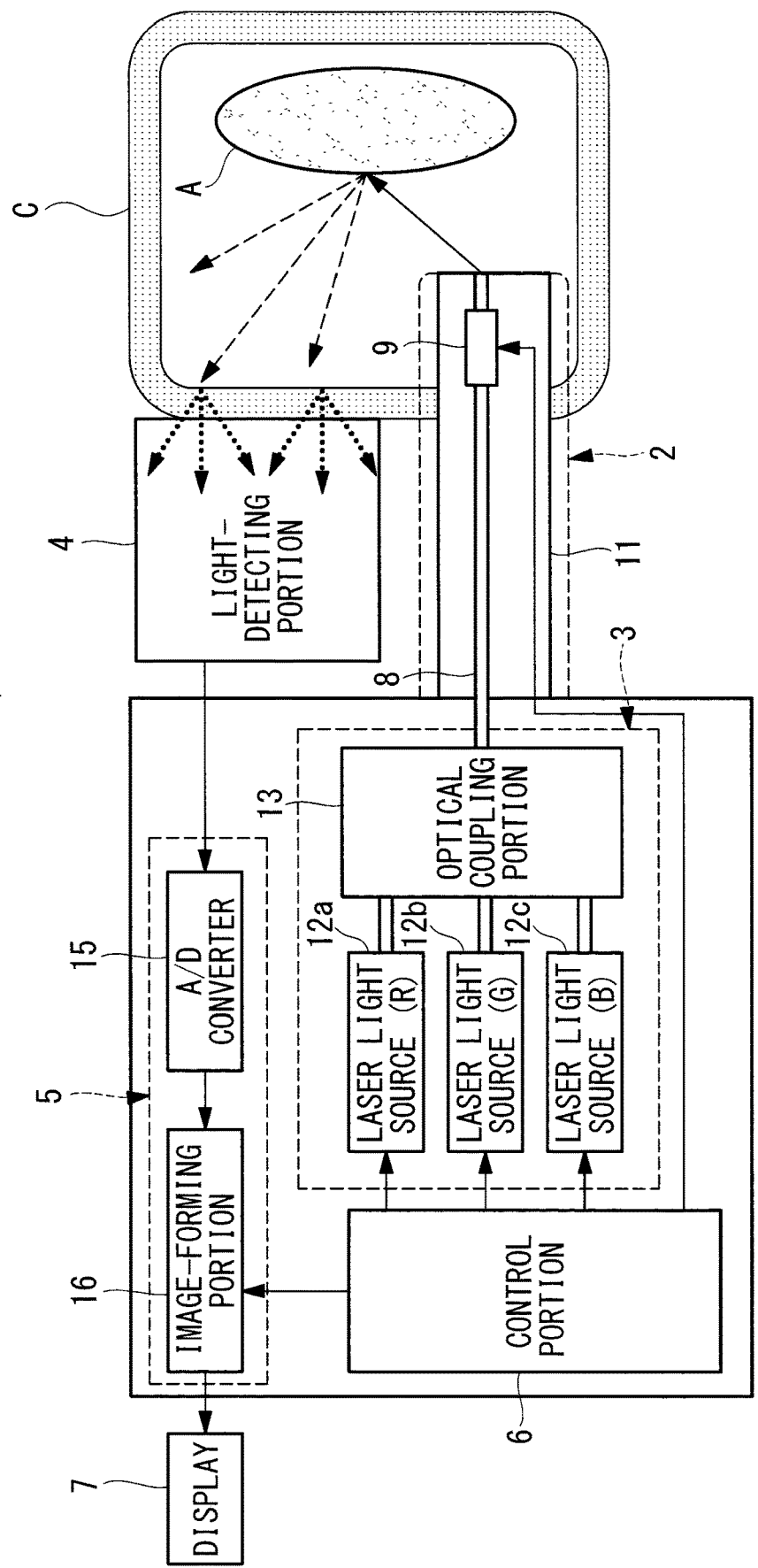
FIG. 1 is a block diagram showing a scanning endoscope system according to an embodiment of the present invention.
Figure 2:
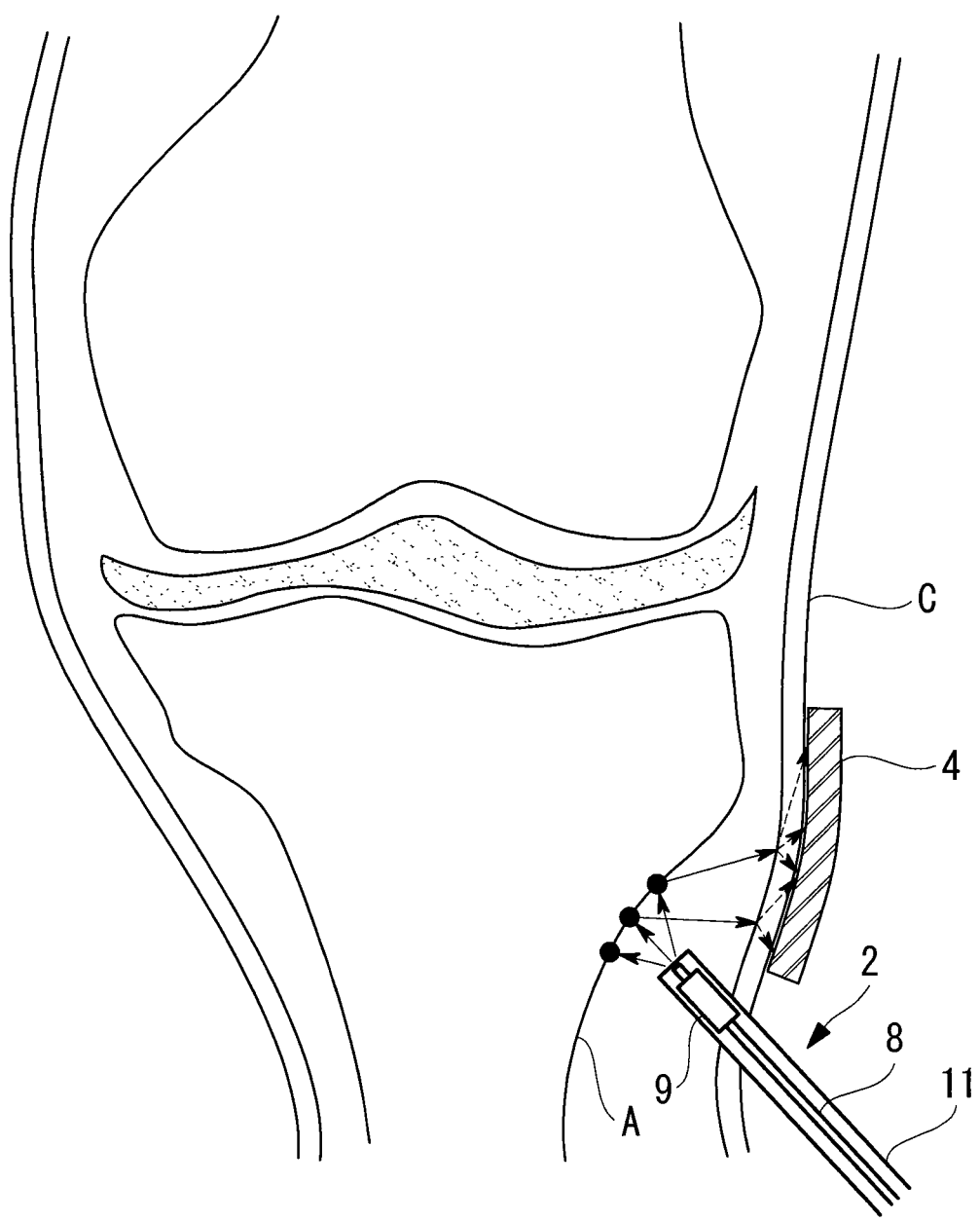
FIG. 2 is a diagram showing an example in which the scanning endoscope system in FIG. 1 is employed.

As shown in FIGS. 1 and 2, the scanning endoscope system 1 according to this embodiment is provided with: an inserted portion (illumination-light emitting portion) 2 that is inserted into a patient; a light-source portion 3 that is connected to the inserted portion 2; a light-detecting portion 4 that is placed in contact with a body surface C of the patient; an image-acquisition portion 5 that acquires an image of an imaging subject A; a control portion 6 that controls the inserted portion 2, the light-source portion 3, and the image-acquisition portion 5; and a display 7 that displays the image acquired by the image-acquisition portion 5.

The inserted portion 2 is provided with: an optical fiber 8 that is disposed at a center portion of the inserted portion 2, that guides light coming from the light-source portion 3, and that is formed of a single-mode fiber; a light-scanning portion 9 that is provided at a distal-end portion of the optical fiber 8 and that two-dimensionally scans light emitted from an emitting end 8a of the optical fiber 8 by causing the emitting end 8a to vibrate; an illumination lens 10 that forms a spot on the imaging subject A by focusing illumination light emitted from the emitting end 8a of the optical fiber 8; and a cylindrical protective member 11 that covers these components.

The light-scanning portion 9 is, for example, a piezoelectric element that generates bending vibrations in accordance with input voltages so as to two-dimensionally vibrate the emitting end 8a of the optical fiber 8 in directions orthogonal to the optical axis.

The first inserted portion 2 will be described in detail by using FIGS. 3 to 5.

Figure 3:
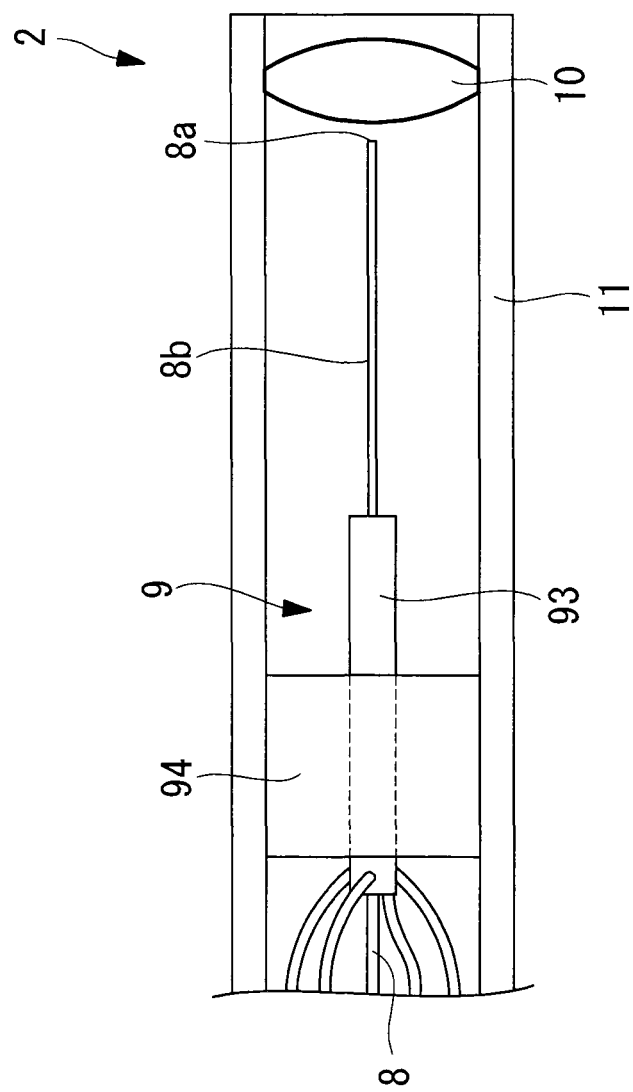
FIG. 3 is a cutaway longitudinal cross-sectional view of a first inserted portion of the scanning endoscope system in FIG. 1.
Figure 4:
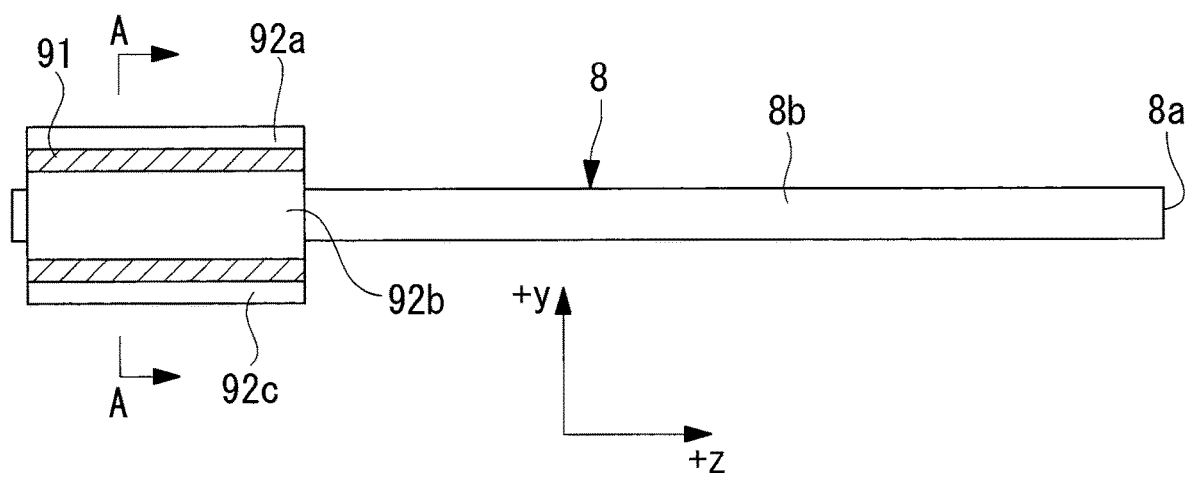
FIG. 4 is a side view of an optical-fiber holding member in the first inserted portion in FIG. 3.

The light-scanning portion 9 is, for example, an actuator that is, as shown in FIGS. 3 and 4, formed of a member that can transmit vibrations and provided with: an optical-fiber holding member 91 that holds the optical fiber 8; piezoelectric elements 92a, 92b, 92c, and 92d that are disposed at the outer circumference of the optical-fiber holding member 91; an actuator tube 93 that covers the piezoelectric elements 92a, 92b, 92c, and 92d and the optical-fiber holding member 91; and an attachment ring 94 that secures the actuator tube 93 to the protective member 11.

As shown in FIG. 4, the optical fiber 8 is supported by the optical-fiber holding member 91, and a portion thereof from the optical-fiber holding member 91 to the emitting end 8a forms a vibrating portion 8b that is vibrated by the piezoelectric elements 92a, 92b, 92c, and 92d.

Figure 5:
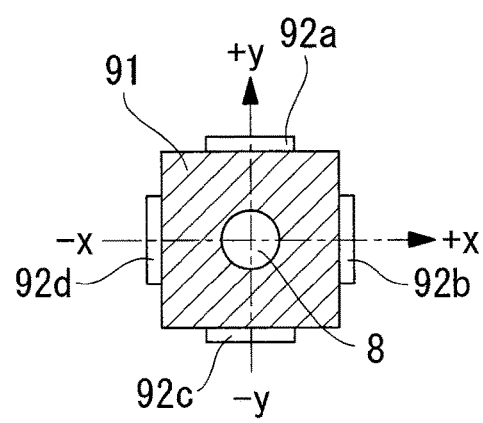
FIG. 5 is a cutaway lateral cross-sectional view of the optical-fiber holding member in FIG. 4.

As shown in FIGS. 4 and 5, the optical-fiber holding member 91 has a quadrangular columnar shape, and each of the four side surfaces thereof is perpendicular to the direction in which light is emitted from the emitting end 8a of the optical fiber 8 (optical-axis direction) and the four side surfaces are also orthogonal to each other. In other words, as shown in FIG. 4, the four side surfaces of the optical-fiber holding member 91 are perpendicular to the +z direction and face the +x direction, +y direction, −x direction, and −y direction, respectively, so as to be orthogonal to each other, as shown in FIG. 5.

Thus, the y-direction-driving piezoelectric elements 92a and 92c that form a pair are secured to the optical-fiber holding member 91 in the +y direction and the −y direction, and the x-direction-driving piezoelectric elements 92b and 92d that form a pair are secured to the optical-fiber holding member 91 in the +x direction and the −x direction. With the pairs of piezoelectric elements that are disposed on either side of the optical-fiber holding member 91 so as to face each other, when one of the piezoelectric elements in the pair is expanded, the other is contracted, which causes deflection in the optical-fiber holding member 91, and thus, by repeating this in an alternating manner, vibrations in the x direction and the y direction are generated, making it possible to cause the emitting end 8a of the optical fiber 8 to perform scanning in a two-dimensional manner. The illumination light emitted from the emitting end 8a of the optical fiber 8 vibrated in this way is focused on the observation subject by the illumination lens 10.

The light-source portion 3 is provided with: three laser light sources (light sources) 12a, 12b, and 12c, such as laser diodes or the like, that emit red light, green light, and blue light, respectively; and an optical coupling portion 13 that combines the light beams of the three colors coming from the laser light sources 12a, 12b, and 12c and guides the light beams to the optical fiber 8. The optical coupling portion 13 is configured by using a fiber-type combiner, a dichroic prism, or the like.

Figure 6:
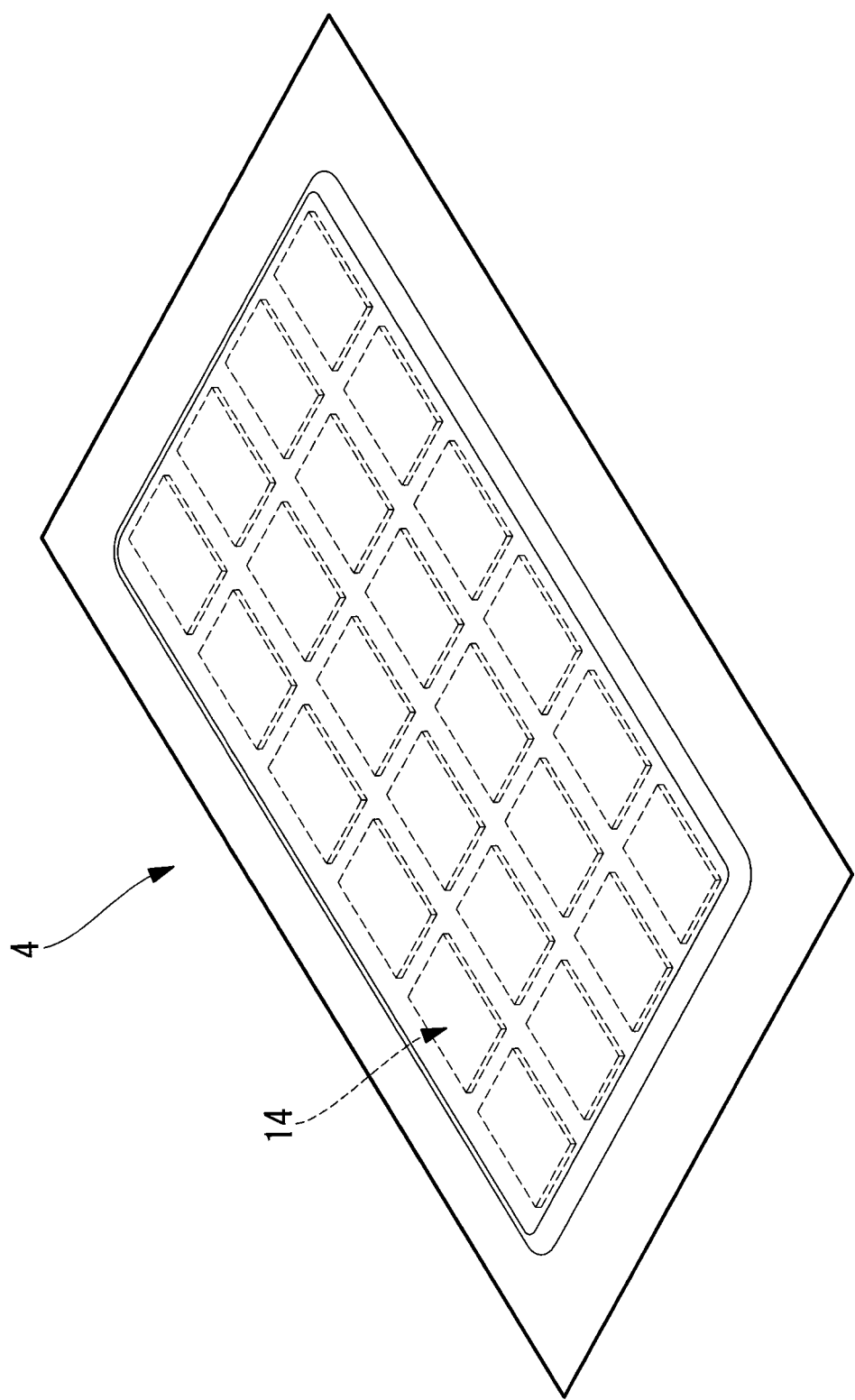
FIG. 6 is a perspective view showing an example of a light-detecting portion in the scanning endoscope system in FIG. 1.
Figure 7:
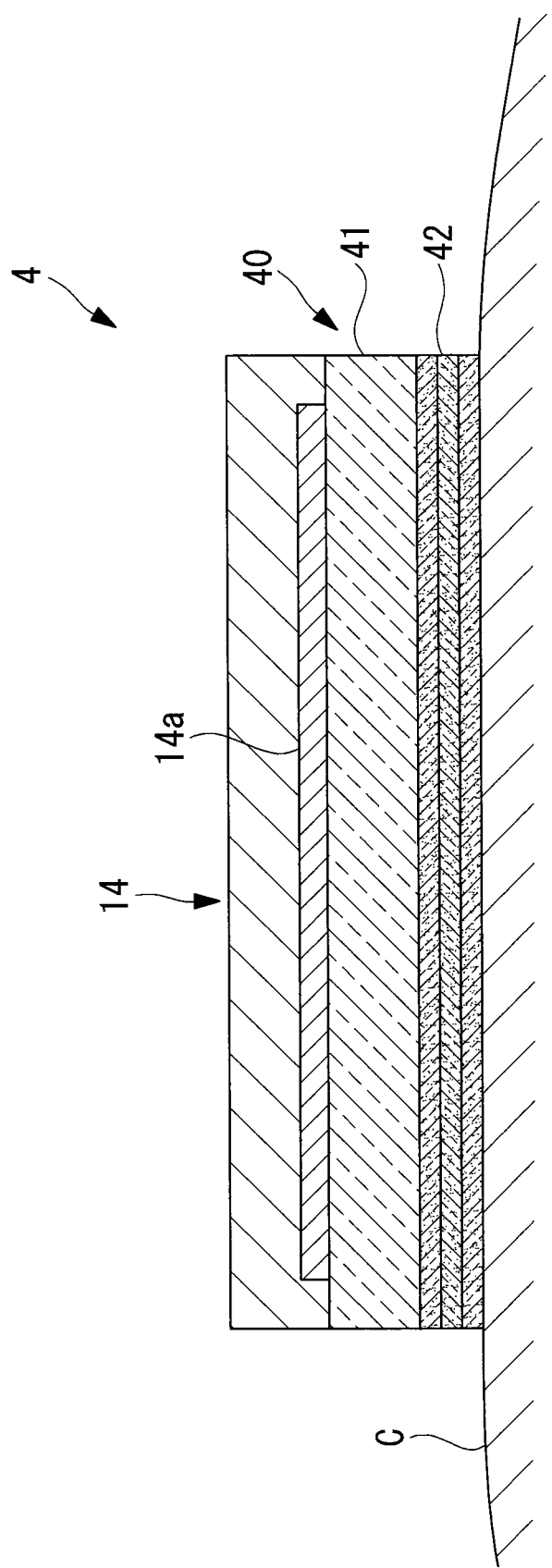
FIG. 7 is a cutaway longitudinal cross-sectional view of a transparent portion in the scanning endoscope system in FIG. 1.

The light-detecting portion 4 is, for example, an adhesive sheet on which a plurality of avalanche photodiodes (detectors) 14 are arranged in an array-like manner, as shown in FIG. 6, and is attached so that light-receiving surfaces 14a of the avalanche photodiodes 14 face the body surface C of the patient. As shown in FIG. 7, transparent portions 40 are provided at the light-receiving surfaces 14a of the avalanche photodiodes 14, and the light-receiving surfaces 14a of the avalanche photodiodes 14 are protected by the transparent portions 40. The individual avalanche photodiodes 14 have sensitivity for the entire wavelength band of the illumination light emitted from the light-source portion 3.

The transparent portions 40 are provided so as to be in close contact with the light-receiving surfaces 14a of the avalanche photodiodes 14, and are constituted of first transparent members 41 (for example, glass, resin, or the like) that are formed of members that can transmit the light coming from the body surface C, and second transparent members 42 that are provided so as to be in close contact with surfaces on the opposite side of the surfaces that are in close contact with the light-receiving surfaces 14a of the avalanche photodiodes 14.

It is preferable that the second transparent members 42 be members that can be placed in close contact with the body surface C while allowing the light coming from the body surface C to pass therethrough, for example, transparent films. The second transparent members 42 that are constituted of a plurality of transparent films are used by attaching the entire surfaces thereof to the body surface C of the patient during observation; the films can be disposed after completing the observation; and, during the subsequent observation, the one transparent film attached to the body surface C is removed and a newly exposed transparent film is attached to the body surface C.

The image-acquisition portion 5 is provided with: an A/D converter 15 that converts analog signals, which are based on the intensity of reflected light detected at the light-receiving surfaces 14a of the avalanche photodiodes 14, to digital signals; and an image-forming portion 16 that forms an image on the basis of the outputs from the A/D converter 15.

The control portion 6 controls the timing at which the laser light sources 12a, 12b, and 12c are turned on, and also controls positions at which the light-scanning portion 9 scans the illumination light beams coming from the respective laser light sources 12a, 12b, and 12c. Furthermore, the control portion 6 transmits, to the image-forming portion 16, information about positions at which the illumination light emitted from the inserted portion 2 is scanned.

The image-forming portion 16 forms an image on the basis of the intensity information of the reflected light output from the A/D converter 15 and the scanning position information of the illumination light transmitted thereto from the control portion 6. The image formed by the image-forming portion 16 is transmitted to the display 7.

The operation of the thus-configured scanning endoscope system 1 according to this embodiment will be described below.

In order to observe the body interior of the patient by using the scanning endoscope system 1 according to this embodiment, first, the light-detecting portion 4 constituted of the adhesive sheet is attached to the body surface of the patient, and, next, the inserted portion 2 is inserted into the body.

When inserting the inserted portion 2 into the body interior, by means of the operation of the control portion 6, three types of illumination light beams are sequentially emitted from the three laser light sources 12a, 12b, and 12c in a predetermined emission order (for example, in order of R, G, and B), and the light-scanning portion 9 is controlled, by means of instruction signals from the control portion 6, thus sequentially changing the scanning positions of the illumination light beams. For example, by means of the operation of the light-scanning portion 9, the emitting end 8a of the optical fiber 8 provided in the inserted portion 2 is moved in a spiraling manner, thus radiating the illumination light beams so that spots thereof are arranged on a spiraling trajectory on the imaging subject A.

As shown in FIG. 1, when the illumination light beams are emitted from the laser light sources 12a, 12b, and 12c, reflected light beams coming from the respective scanning positions in the imaging subject A in the body pass through the body tissue (medium) covering the imaging subject A and are emitted outside from the body surface, and a portion thereof enters the light-receiving surfaces 14a in the avalanche photodiodes 14 of the light-detecting portion 4, which is attached on the body surface in advance, and thus, this light is detected. The intensity information of the reflected light beams detected by the light-detecting portion 4 is transmitted to the image-forming portion 16 after being converted to digital signals by the A/D converter 15.

Because the information about the scanning positions of the spots of the illumination light beams in the imaging subject A, which corresponds to the intensity information of the reflected light beams, is transmitted to the image-forming portion 16 from the control portion 6, the image-forming portion 16 can generate a two-dimensional color image by arranging the intensity information of the detected reflected light beams so as to correspond to the scanning positions.

Figure 8:
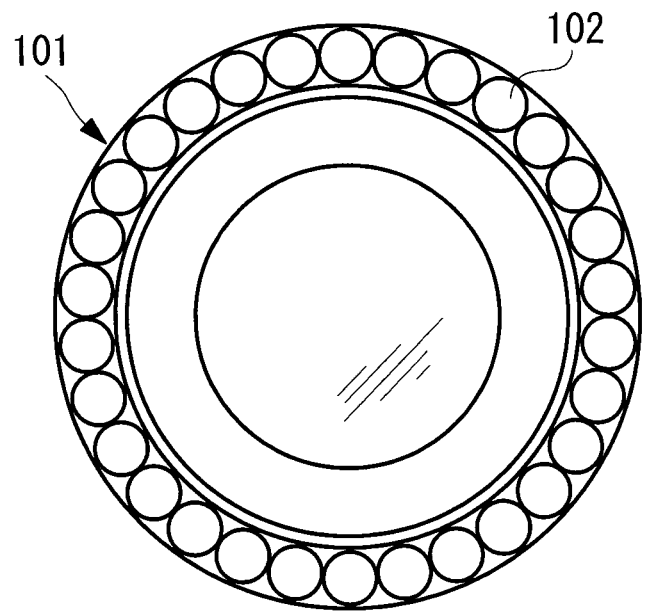
FIG. 8 is a front view showing an inserted portion in a conventional scanning endoscope.
Figure 9:
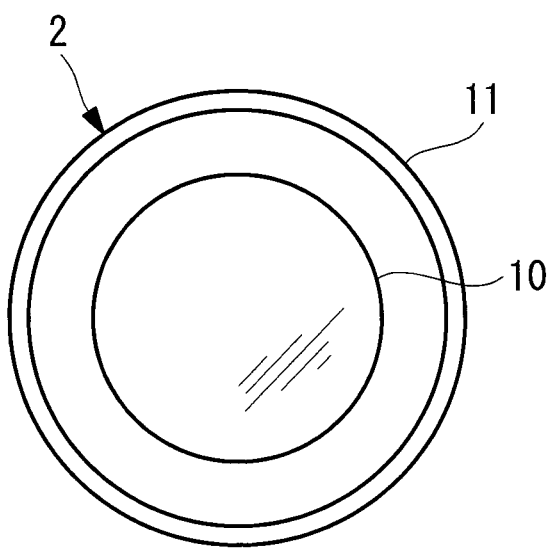
FIG. 9 is a front view showing an inserted portion in the scanning endoscope system in FIG. 1.

In this case, with the scanning endoscope system 1 according to this embodiment, the light-detecting portion 4 is attached to the body surface as a separate piece from the inserted portion 2 that is inserted into the body. Therefore, as compared to a conventional inserted portion 101 shown in FIG. 8 as a comparative example, as shown in FIG. 9, it is possible to decrease the outer diameter of the inserted portion 2 by eliminating a light-receiving optical fiber 102 in the inserted portion 2, and thus, there is an advantage in that it is possible to decrease the invasiveness to the patient.

Note that, in this embodiment, the reflected light beams of the illumination light beams emitted from the inserted portion 2, reflected at the imaging subject A, are detected outside the body of the patient, and the light beams having the wavelengths that are substantially equivalent to the wavelengths of the illumination light beams are detected. Because it is possible to detect the light beams having the wavelengths that are substantially the same as those of the illumination light beams returning from the imaging subject A, it is possible to perform observation by directly using the information obtained at the wavelengths of the illumination light beams, and thus, it is possible to obtain a high-precision image. In addition, loss of light is low, and thus, it is possible to obtain a bright image.

Because of this, it is preferable to employ configurations such as those described below.

First, it is preferable that the light levels of the illumination light beams emitted from the respective laser light sources 12a, 12b, and 12c of the light-source portion 3 be determined in accordance with the transmittances of the reflected light beams in the body tissue.

In other words, the imaging subject A in the body is covered by the body tissue (medium), and the reflected light beams from the imaging subject A are detected by the light-detecting portion 4 after passing through the body tissue. Although the reflected light beams are attenuated while passing through the body tissue, the transmittances thereof differ for each of the wavelengths. Because of this, radiating the illumination light beams at uniform light levels at all wavelengths causes the light-level balance to be deteriorated in the reflected light beams at the time of detection by the light-detecting portion 4.

Figure 10:
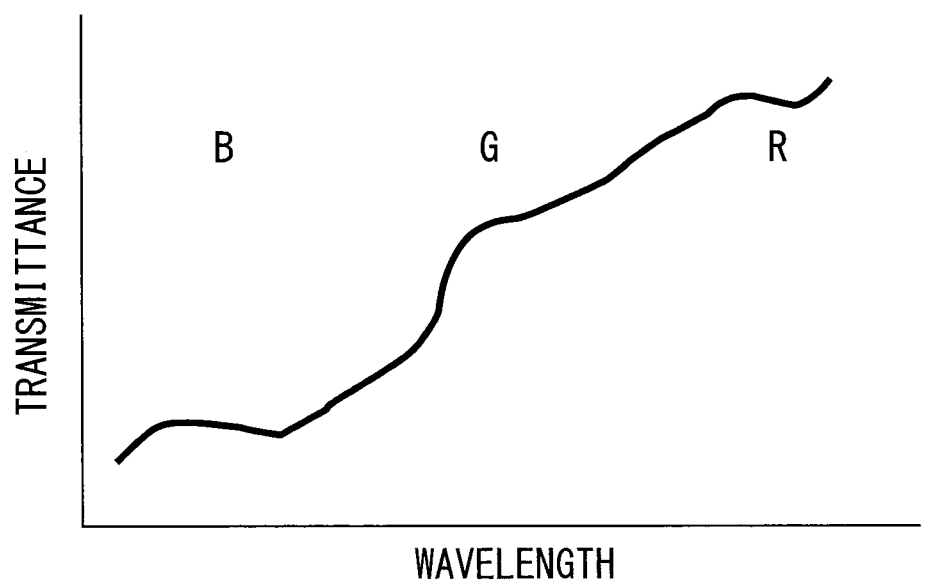
FIG. 10 is a diagram showing a wavelength distribution of light transmittance in body tissue.

Specifically, as shown in FIG. 10, the transmittances of the reflected light beams in the body tissue are 0.3 for red light R (wavelength of approximately 600 nm), 0.2 for green light G (wavelength of approximately 540 nm), and 0.1 for blue light B (wavelength of approximately 430 nm). The light-level balance of the illumination light beams emitted from the laser light sources 12a, 12b, and 12c is determined in accordance with the transmittances for each of the wavelengths. Specifically, the light level of the illumination light beam is decreased for the wavelength at which the transmittance is greater, and the light level of the illumination light beam is increased for the wavelength at which the transmittance is lower. Therefore, the light-level ratio of the illumination light beams emitted from the respective laser light sources 12a, 12b, and 12c having the three colors, that is, R, G, and B, is set to be R:G:B=3.3:5:10. By doing so, the reflected light beams are detected in an appropriate light-level balance, and thus, there is an advantage in that is it possible to enhance the image quality by enhancing the SN ratio (SNR: signal to noise ratio) for the blue light which has the lowest transmittance, and that it is possible to acquire an image having high color reproducibility.

In this Example, the light-level ratio is set so as to be the inverse of the transmittance ratio among the respective wavelengths, namely, R:G:B=3:2:1, in other words, the light-level ratio is set to be R:G:B=1/3:1/2:1; however, there is no limitation thereto, and it suffices that the light level of the illumination light beam be decreased for the wavelength at which the transmittance is greater, and the light level of the illumination light beam be increased for the wavelength at which the transmittance is lower, and thus, it is permissible to set the light level ratio to be, for example, a squared ratio, namely, R:G:B=1/9:1/4:1, or a square-root ratio, namely, R:G:B=1/$\sqrt{3}$:1/$\sqrt{2}$:1. In the Examples hereinafter, when setting the light-level balance and the area ratio, setting thereof may be performed in accordance with the relative magnitude relationship of parameters (transmittance, sensitivity) that serve as determinants of the light-level balance and the area ratio with respect to the each of the wavelengths. The manner in which concrete values are determined when doing so may be set in accordance with squared values, square roots, or the like, without limitation to a simple inverse proportion as in this Example (the light-level balance is set in accordance with the transmittances).

For example, in the case in which there is an upper limit in the light source device, there is no need to accurately match the transmittance ratio with this ratio, and the transmittance ratio may be set to be values equal to or less than the upper limit. Specifically, when the transmittance ratio among the respective wavelengths is R:G:B=3:2:1, setting the light-level ratio so as to be the inverse of the transmittance ratio, that is, R:G:B=1/3:1/2:1, gives the values 3.3 mW, 5.0 mW, and 10 mW; however, when the upper limit of the light source is 8 mW, having the values 3.3 mW, 5.0 mW, and 8.0 mW presents no problem because the magnitude relationship among the respective wavelengths is maintained.

Figure 11A:
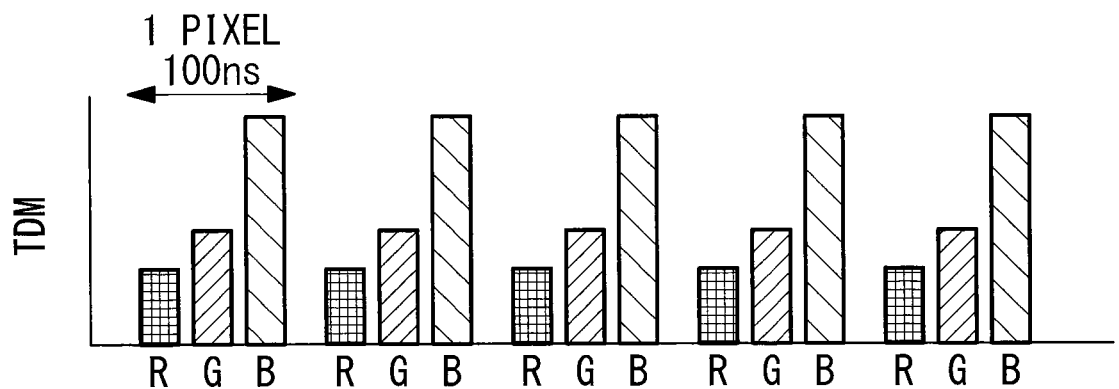
FIG. 11A is a diagram showing irradiation patterns of illumination light beams emitted from individual laser light sources provided in a light-source portion in the scanning endoscope system in FIG. 1, in the case in which a TDM method is employed.
Figure 11B:
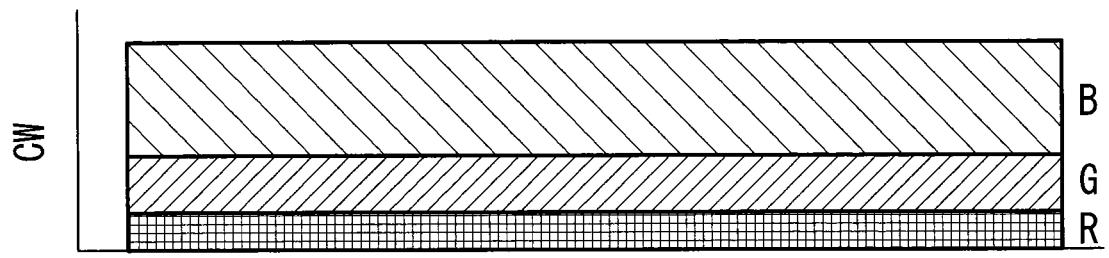
FIG. 11B is a diagram showing irradiation patterns of the illumination light beams emitted from the individual laser light sources provided in the light-source portion in the scanning endoscope system in FIG. 1, in the case in which a CW method is employed.
Figure 11C:
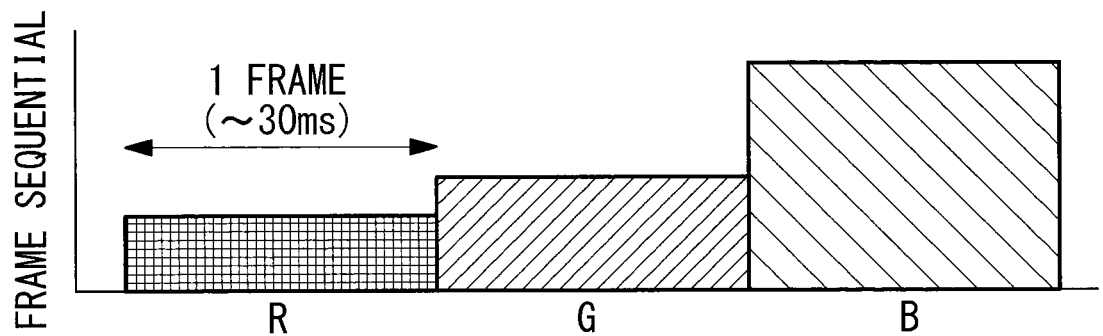
FIG. 11C is a diagram showing irradiation patterns of the illumination light beams emitted from the individual laser light sources provided in the light-source portion in the scanning endoscope system in FIG. 1, in the case in which a frame sequential method is employed.

FIGS. 11A, 11B, and 11C show methods of setting, as has been described above, the light-level ratio of the illumination light beams coming from the respective laser light sources 12a, 12b, and 12c. In all of the methods in FIG. 11, that is, a TDM (time division multiplexing) method in FIG. 11A in which emission of the illumination light beams of the three colors is sequentially switched for each pixel, a CW method in FIG. 11B in which the illumination light beams of the three colors are constantly emitted, and a frame sequential method in FIG. 11C in which emission of the illumination light beams of the three colors is sequentially switched for each frame, it is permissible to employ a method in which the light-level ratio of the illumination light beams emitted from the respective laser light sources 12a, 12b, and 12c is set so as to be the above-described ratio.

In addition, with the CW method, because it is necessary to separately detect the individual wavelengths in the light-detecting portion 4, it is necessary to provide optical filters for each of the wavelengths, which are used to separate the wavelengths, and the avalanche photodiodes 14 for each of the wavelengths, which are used to detect individual components of the separated light.

The intensity information of the reflected light beams detected by the light-detecting portion 4 for the respective wavelengths is transmitted to the image-forming portion 16 after being converted to the digital signals by the A/D converter 15.

Because the information about the scanning positions of the spots of the illumination light beams in the imaging subject A, which corresponds to the intensity information of the reflected light beams for the respective wavelengths, is transmitted to the image-forming portion 16 from the control portion 6, the image-forming portion 16 can generate a two-dimensional color image by arranging the colors of the detected reflected light beams and the intensity information so as to correspond to the scanning positions.

Second, it is preferable that the light levels of the illumination light beams emitted from the respective laser light sources 12a, 12b, and 12c of the light-source portion 3 be determined in accordance with the light-receiving sensitivities of the detectors 14 of the light-detecting portion 4.

Figure 12:
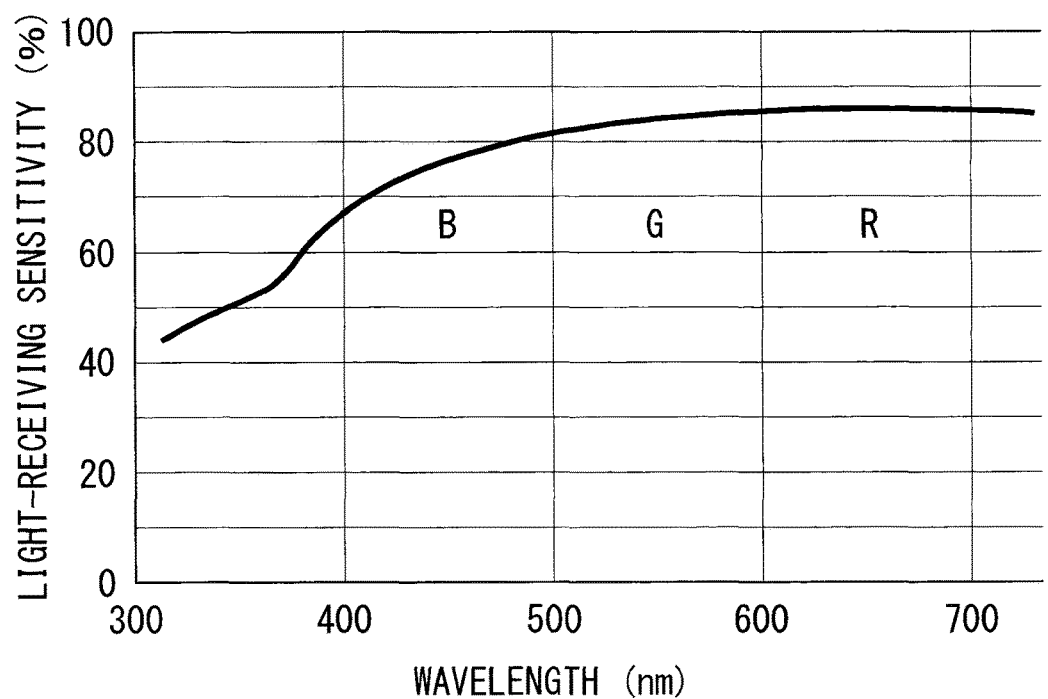
FIG. 12 is diagram showing wavelength characteristics with respect to the light-receiving sensitivity of a detector provided in the light-detecting portion in the scanning endoscope system in FIG. 1.

In other words, with the detectors such as the avalanche photodiodes 14, the light-receiving sensitivities differ for each of the wavelengths, as shown in FIG. 12. Because of this, radiating the illumination light beams at uniform light levels in all wavelengths causes the light-level balance to be deteriorated in the reflected light beams detected by the light-detecting portion 4.

Specifically, the light-receiving sensitivities of the detectors 14 for the respective wavelengths are such that R:G:B=1.0:0.9:0.8, as shown in FIG. 12. Because the transmittances in the body tissue are such that R:G:B=0.3:0.2:0.1, as described above, by calculating the inverse by multiplying these values with each other, the light-level ratio of the illumination light beams emitted from the respective laser light sources 12a, 12b, and 12c having the three colors, namely, R, G, and B is set to be R:G:B=1/0.3:1/0.18:1/0.08. By doing so, the SN ratio of the blue light for which the transmittance is the lowest and the light-receiving sensitivity is also the lowest is enhanced, and thus, there are also the advantages that it is possible to further enhance the image quality, and it is also possible to further enhance the color reproducibility.

For example, because it is not possible to unlimitedly increase the light level when a system has an upper limit to the total amount of the illumination light level, it is necessary to appropriately allocate light levels to the respective colors. At this time, by allocating a high light level to the color for which the SN ratio tends to be deteriorated the most, it is possible to improve the SN ratio of that color, and, because this eliminates an extreme deterioration of the SN ratio when a color image is generated, it is possible to enhance the image quality.

Third, in the case in which the detectors in the light-detecting portion 4 are provided by arranging the plurality of avalanche photodiodes 14 in an array-like manner, it is preferable that the ratio of the numbers of the three types of avalanche photodiodes 14 (for example, those in which three types of filters (for R, G, and B) are attached to the light-receiving surfaces of the avalanche photodiodes 14) having different light-receiving sensitivities for different wavelengths, in other words, the ratio of the light-receiving areas, be determined in accordance with the transmittances of the reflected light beams in the body tissue.

Figure 13:
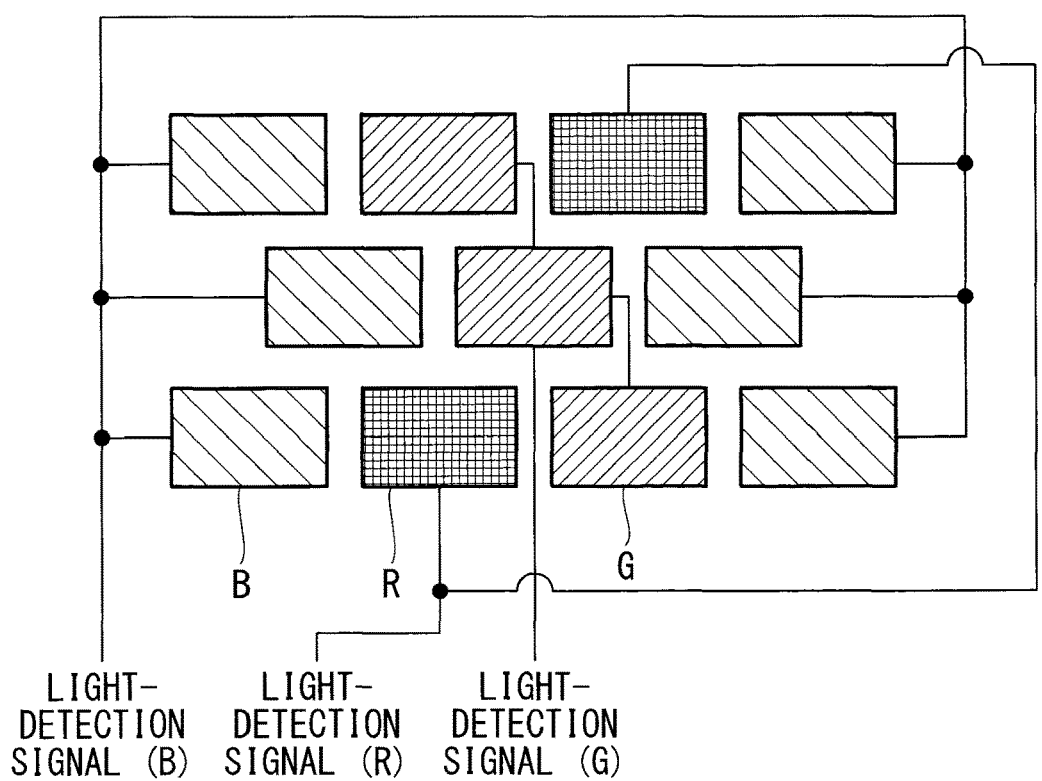
FIG. 13 is a diagram showing, in the light-detecting portion in the scanning endoscope system in FIG. 1, an example of arraying of detectors in which light-receiving areas are adjusted in accordance with light transmittances in body tissue for separate wavelengths.

Specifically, in the above example, in the case in which the transmittances in the body tissue are such that R:G:B=0.3:0.2:0.1, by taking the inverses thereof, the ratio of the number of avalanche photodiodes 14 is set to be R:G:B=2:3:6, as shown in FIG. 13. By doing so, even in the case in which the illumination light beams of the three colors at uniform light levels are emitted from the light-source portion 3, there is an advantage in that it is possible to enhance the image quality by enhancing the SN ratio of the blue light for which the transmittance is the lowest, and that it is also possible to enhance the color reproducibility. Note that, at this time, the light-detecting portion 4 is provided for each wavelength, and the reflected light beams are detected by summing up the reflected light beams for the respective wavelengths.

In addition, the ratio of the light-receiving areas may be determined in accordance with the light-receiving sensitivities of the detectors 14 of the light-detecting portion 4. By doing so, even in the case in which the illumination light beams of the three colors at uniform light levels are emitted from the light-source portion 3, there is an advantage in that it is possible to enhance the image quality by enhancing the SN ratio of the blue light for which the transmittance is the lowest, and that it is also possible to enhance the color reproducibility.

Furthermore, the ratio of the light-receiving areas may be determined by multiplying the light-receiving sensitivity with the transmittance. In this case also, even in the case in which the illumination light beams of the three colors at uniform light levels are emitted from the light-source portion 3, there is an advantage in that it is possible to enhance the image quality by enhancing the SN ratio of the blue light for which the transmittance is the lowest, and that it is also possible to enhance the color reproducibility.

Figure 14:
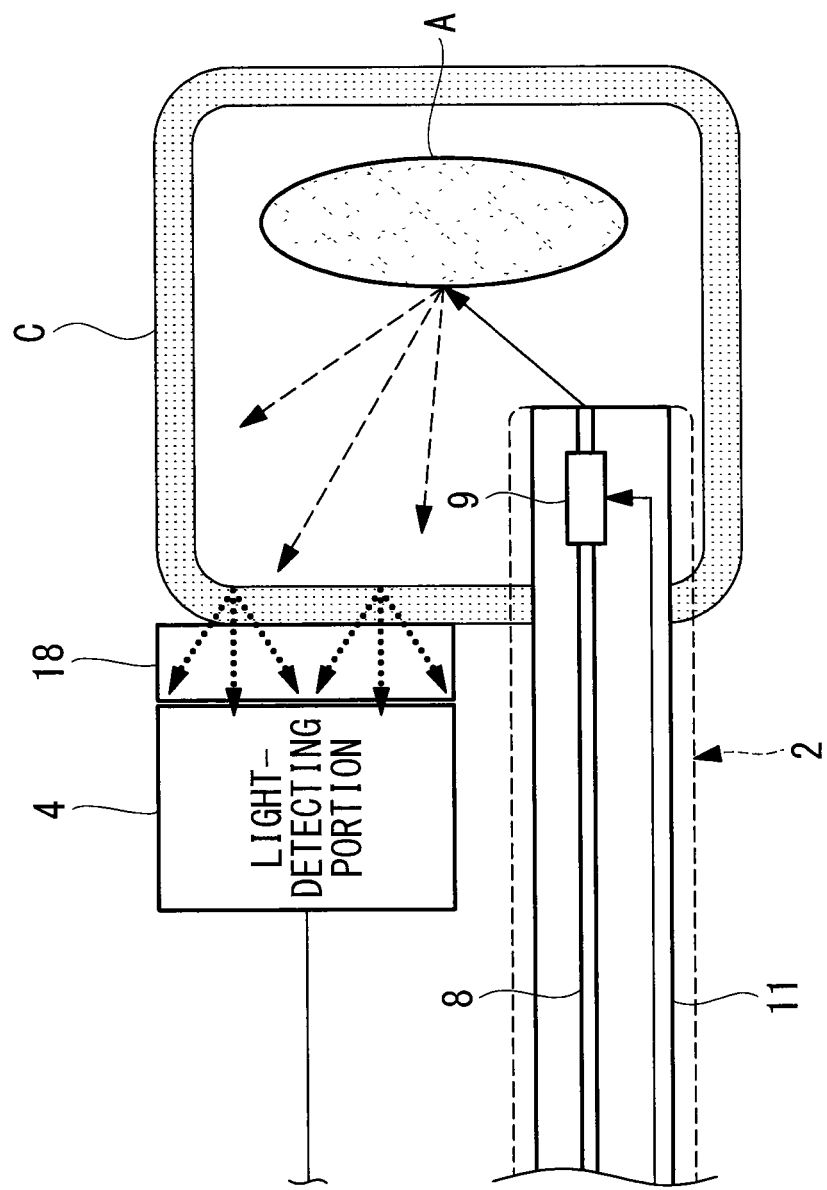
FIG. 14 is a partial schematic view, showing a modification of the scanning endoscope system in FIG. 1, for explaining a case in which a band-pass filter is disposed in a preceding stage of the light-detecting portion.

Fourth, as shown in FIG. 14, it is preferable that a band-pass filter 18 that transmits light in the wavelength bands of the illumination light beams and that blocks light in other wavelength bands be disposed in a preceding stage of the light-detecting portion 4. By doing so, it is possible to block external light or stray light having wavelengths other than those in the wavelength bands of the illumination light beams, and thus, it is possible to acquire an image having low noise.

Because the reflected light that is released from body tissue and that is coming from the imaging subject A is diffused from the body surface C, it is preferable that the band-pass filter 18 be in close proximity to the body surface C. In addition, an optical system for focusing the diffuse light coming from the body surface C onto the light-detecting portion 4 may be disposed between the body surface C and the band-pass filter 18, or a light-detection optical fiber that guides the diffuse light coming from the body surface C to the light-detecting portion 4 may be disposed between the body surface C and the band-pass filter 18.

Figure 15:
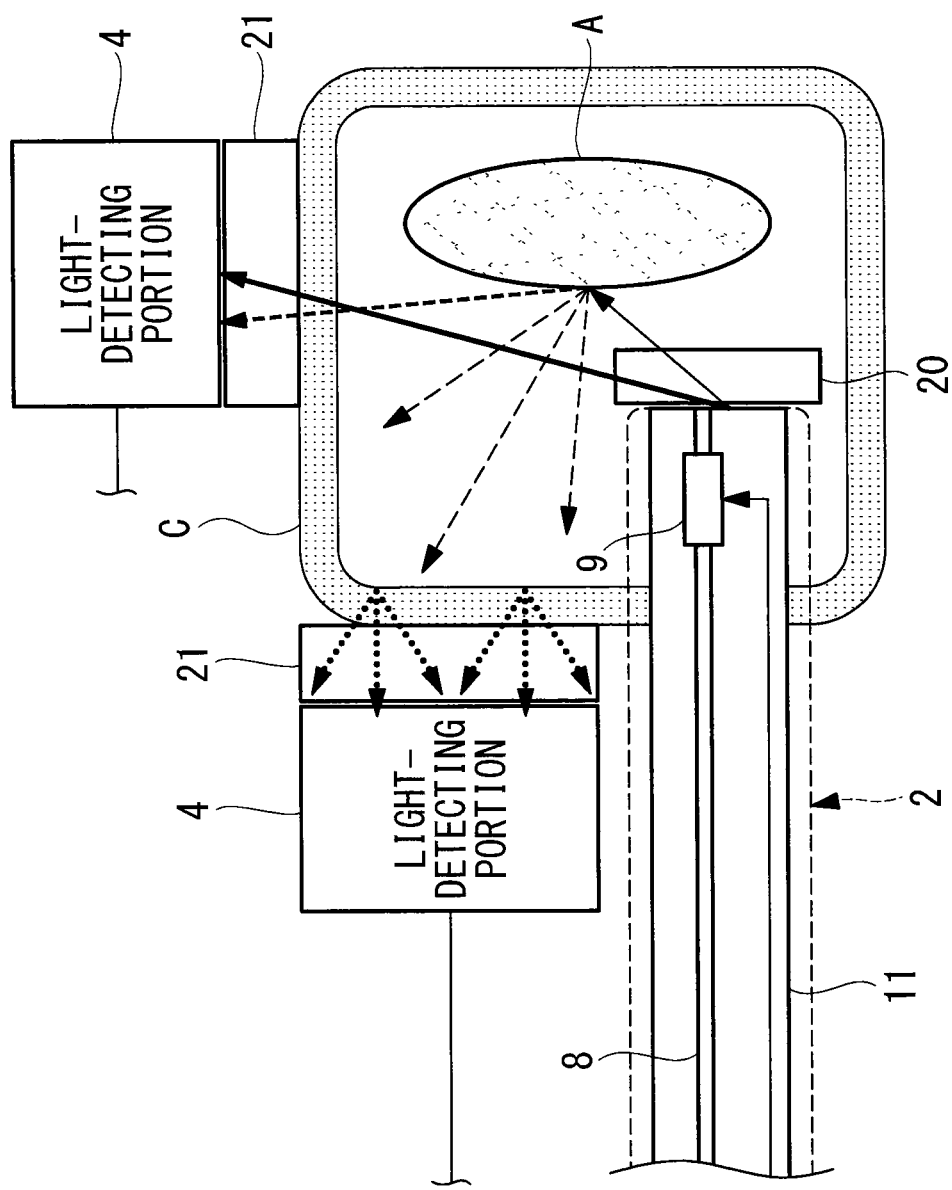
FIG. 15 is a diagram showing another modification of the scanning endoscope system in FIG. 1, for explaining a case in which a polarizing member is provided.
Figure 16:
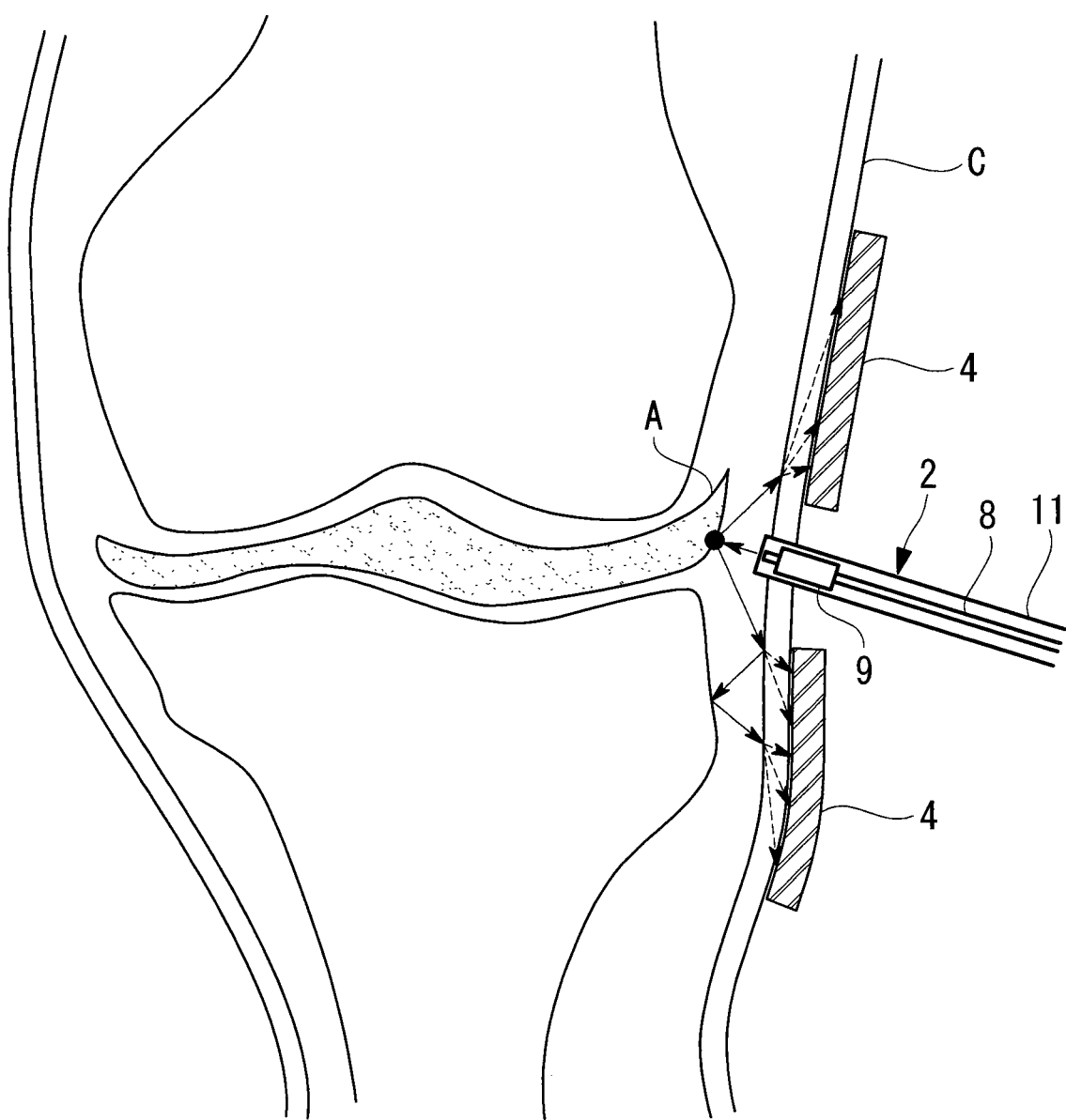
FIG. 16 is a diagram showing an example in which the scanning endoscope system in FIG. 15 is employed.

Fifth, as shown in FIGS. 15 and 16, it is preferable that a first polarizing member (polarizing member) 20 that aligns the polarization direction with a first polarization direction when allowing the illumination light beams to pass therethrough be provided at a distal end of the inserted portion 2 from which the illumination light beams are emitted, and that a second polarizing member (polarizing member) 21 that blocks the illumination light beams having the first polarization direction and that allows the illumination light beams having other polarization directions to pass therethrough be provided in a preceding stage of the light-detecting portion 4. The first polarizing member 20 is, for example, a $\lambda/2$ plate, and the second polarizing member 21 is a polarization beam splitter. Note that the light-detecting portions 4 and the band-pass filters 18 are provided at multiple locations.

By doing so, depending on the angle at which the inserted portion 2 is inserted, it is possible to block, by means of the second polarizing member 21, the illumination light that is emitted from the inserted portion 2 and that directly enters the light-detecting portion 4 without being radiated onto the imaging subject A. On the other hand, because the polarization state of the reflected light reflected at the imaging subject A is changed by being affected by biological scattering when being reflected, the reflected light passes through the second polarizing member 21, and it is possible to detect the reflected light by using the light-detecting portion 4. By doing so, it is possible to acquire an image having low noise by preventing detection of the illumination light that directly enters the light-detecting portion 4 instead of by way of the imaging subject A. Here, the illumination light coming from the illumination optical fiber 8 possesses linear polarization to begin with, or it is not necessarily required to provide the first polarizing member 20 if the illumination optical fiber 8 is changed to a polarization maintaining fiber.

In addition, in the case in which the surface of the imaging subject A is relatively mirror-like and flat, a $\lambda/4$ plate may be employed as the first polarizing member 20, and a linearly polarizing plate may be employed as the second polarizing member 21. When the illumination light coming from the illumination optical fiber 8 is radiated onto the imaging subject A after being converted to circularly polarized light by means of the $\lambda/4$ plate 20, the s polarization component is increased in the reflected light coming from the imaging subject A as compared with the p polarized light. By installing the linearly polarizing plate 21 provided in the light-detecting portion 4 so as to be oriented in a direction in which p polarized light is blocked and s polarized light is allowed to pass therethrough, it is possible to allow the reflected light coming from the imaging subject A to pass therethrough and to block the p polarization component of the illumination light that directly enters the light-detecting portion 4 without being radiated onto the imaging subject A. Therefore, it is possible to acquire an image having low noise as compared to before installing the first polarizing member 20 and the second polarizing member 21.

Sixth, in addition to being provided with the three types of laser light sources, namely, R, G, and B, as the laser light sources 12a, 12b, and 12c, the light-source portion 3 may be provided with a laser light source that emits near-infrared or infrared illumination light.

By doing so, although the reflected light beams in the RGB wavelength bands are greatly attenuated in the case in which the body tissue that covers the imaging subject A is thick, near-infrared or infrared reflected light having high transmittance is detected even in such a case, and thus, there is an advantage in that it is possible to clearly visualize the structure of the imaging subject A.

In addition, although this embodiment has been described in terms of an example in which the piezoelectric elements 92a, 92b, 92c, and 92d are employed as the light-scanning portions 9, the method by which the illumination light is scanned is not limited thereto, and an electromagnetic induction method or a method using a galvanometer mirror may be employed.

In addition, although the adhesive sheet on which the avalanche photodiodes 14 are arranged in an array-like manner has been described as an example of the light-detecting portion 4, alternatively, a light-receiving end of a fiber bundle may be attached to a body surface of a patient by using transparent adhesive. In this case, providing one light-detecting portion 4 is sufficient.

In the case in which the light-receiving end of the fiber bundle is installed at the body surface so as to serve as the light-detecting portion 4, the area of the bundle end surface may be adjusted in order to adjust the light-receiving areas for the respective wavelengths described in the various Examples described above.

Figure 17:
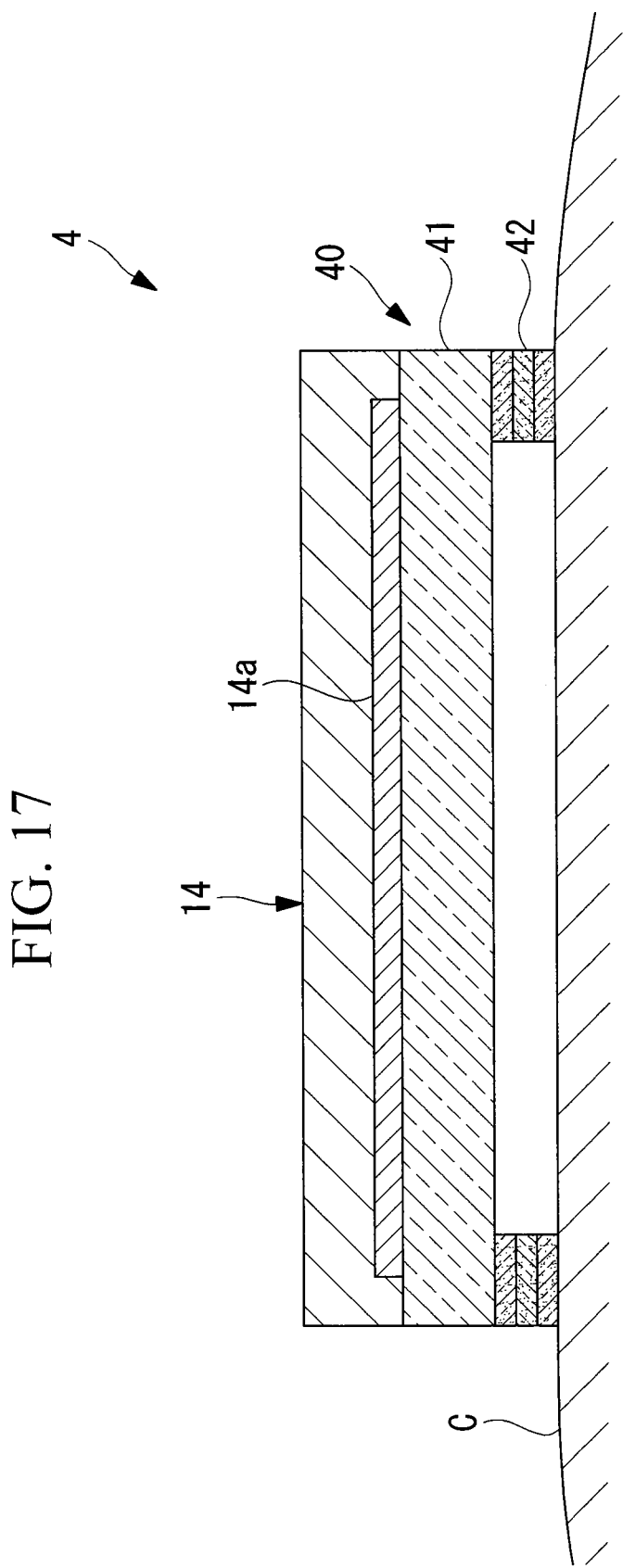
FIG. 17 is a diagram showing a modification of the scanning endoscope system in FIG. 1, which is an example in which a second transparent member is attached only along an edge of a first transparent member.

In addition, although this embodiment has been described in terms of an example in which the entire surface of the second transparent member 42 is attached to the body surface C by being brought into direct contact therewith, alternatively, as shown in FIG. 17, a member that is attached only along an edge of the first transparent member 41 may be employed. In this case, when the second transparent member 42 is attached to the body surface C by being brought into close contact therewith, a gap is created between the body surface C and the first transparent member 41.

In addition, although an example in which the second transparent member 42 is formed of a plurality of transparent films has been described, a single transparent film may be used.

Figure 18:
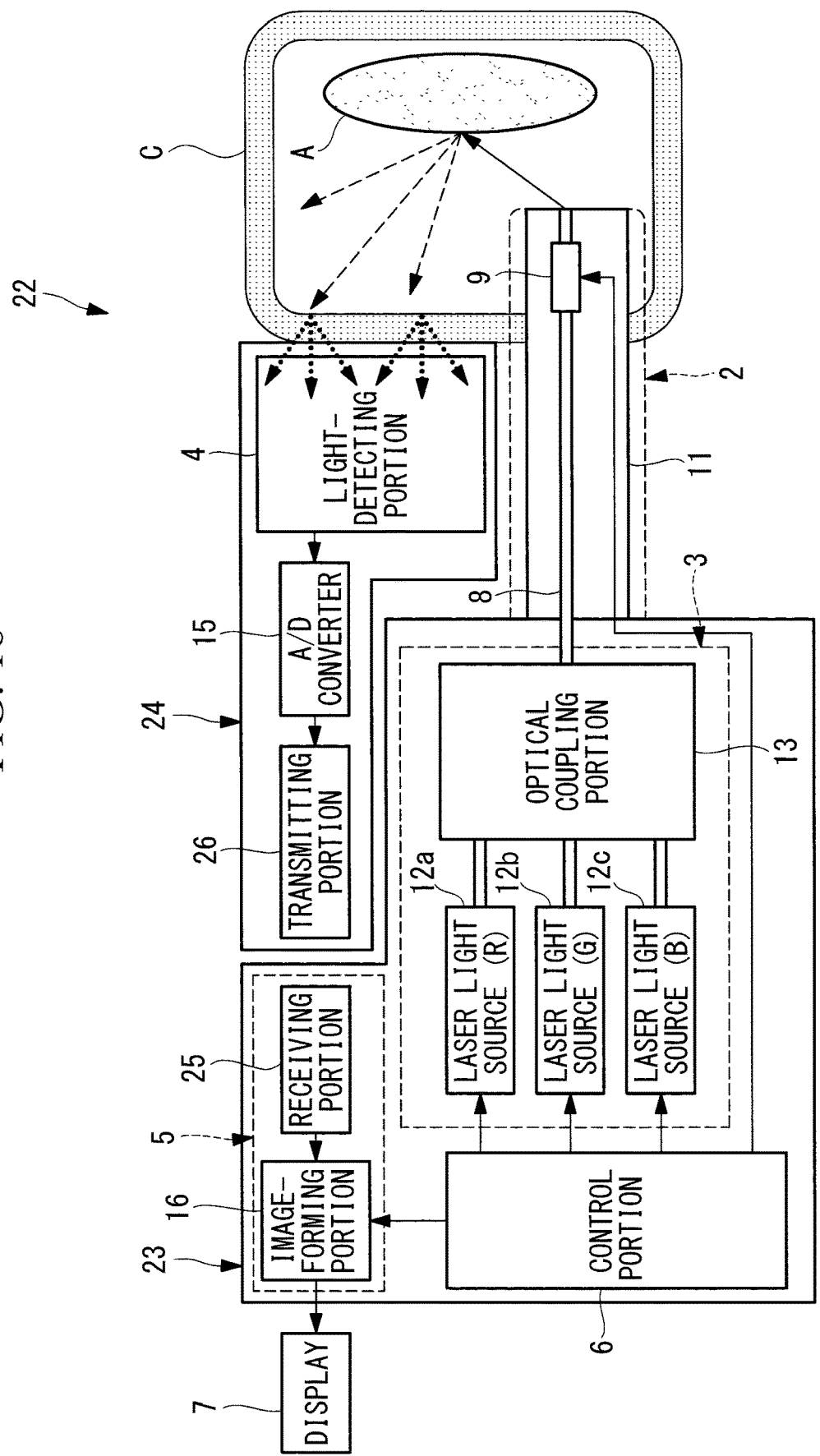
FIG. 18 is a diagram showing a modification of the scanning endoscope system in FIG. 1, which is an example in which the inserted portion and the light-detecting portion are wirelessly connected.

In addition, although the inserted portion 2 from which the illumination light is emitted and the light-detecting portion 4 that detects the reflected light may be connected by a wire, as shown in FIG. 18, the digital signals may be transmitted and received wirelessly.

Specifically, it is permissible to employ a scanning endoscope system 22 provided with: a first endoscope system (scanning endoscope system) 23 provided with the inserted portion 2, the light-source portion 3, the control portion 6, the image-forming portion 16, and a receiving portion 25; a second endoscope system 24 provided with the light-detecting portion 4, the A/D converter 15, and a transmitting portion 26; and the display 7.

With the second endoscope system 24, the light that is emitted from the inserted portion 2 and reflected at the imaging subject is detected by the light-detecting portion 4, and the intensity information of the detected reflected light is transmitted to the transmitting portion 26 after being converted to digital signals by the A/D converter 15.

The transmitting portion 26 transmits the digital signals transmitted thereto from the A/D converter 15. Then, the digital signals transmitted from the transmitting portion 26 are received by the receiving portion 25 of the first endoscope system 23, the received digital signals are transmitted to the image-forming portion 16 to generate an image, and the generated image is displayed on the display 7.

By wirelessly connecting the first endoscope system 23 and the second endoscope system 24 in this way, it is possible to enhance the degree of freedom of the attaching position in the body surface C of the patient without depending on the first endoscope system 23 or causing problems such as a cable becoming entangled or the like.

Note that the transmitting portion 26 and the receiving portion 25 may be disposed anywhere in the first endoscope system 23 and the second endoscope system 24, respectively.

In addition, without limitation to providing one, it is permissible to provide a plurality of the light-detecting portions 4, which are disposed at the body surface of the patient, in accordance with the shape of the body surface. In the case in which a plurality of light-detecting portions 4 are provided, a plurality of the same types of photodetectors 4 may be provided, or it is permissible to provide a plurality of photodetectors having different light-receiving areas or photodetectors for the respective wavelengths (for example, those individually provided with R, G, and B filters).

As a result, the above-described embodiment leads to the following aspect.

An aspect of the present invention is a scanning endoscope system including: an illumination-light emitting portion that is inserted into a body of a patient and that emits illumination light emitted from a light-source portion toward an imaging subject in the body in a spot-like manner; a light-scanning portion that scans the illumination light on the imaging subject; and a light-detecting portion that is disposed at a body surface of the patient, and that detects reflected light coming from the scanning position in the imaging subject, at which the illumination light is scanned by the light-scanning portion.

With this aspect, when the illumination light emitted from the light-source portion is scanned by the light-scanning portion and emitted, in a spot-like manner, toward the imaging subject in the body from the illumination-light emitting portion inserted into the body of the patient, the reflected light coming from the imaging subject is released outside the body of the patient by passing through the medium covering the imaging subject, and is detected by the light-detecting portion disposed at the body surface.

Because the light-detecting portion that detects the reflected light coming from the scanning position in the imaging subject is disposed outside the body as a separate piece from the illumination-light emitting portion, it is possible to decrease the diameter of the portion that is inserted into the body of the patient, and thus, it is possible to observe the reflected light returning from the imaging subject while decreasing the invasiveness to the patient.

In the above-described aspect, the light-detecting portion may detect the reflected light having a wavelength that is substantially equivalent to that of the illumination light.

In the above-described aspect, the light-source portion may be provided, and the light-source portion may be provided with a plurality of light sources that emit a plurality of illumination light beams having different wavelengths.

In the above-described aspect, a light-level balance of the illumination light beams emitted from the respective light sources may be determined so as to be decreased with an increase in transmittances of the reflected light beams between the imaging subject and the light-detecting portion for respective wavelengths.

By doing so, the illumination light beams emitted from the respective light sources of the light-source portion are reflected at the imaging subject in the body and are subsequently detected by the light-detecting portion disposed at the body surface of the patient by passing through the medium covering the imaging subject. Although the reflected light beams in the imaging subject are attenuated when passing through the medium, the degree of transmission differs depending on the wavelengths.

In the above-described aspect, a light-level balance of the illumination light beams emitted from the respective light sources may be determined so as to be decreased with an increase in light-receiving sensitivities between the imaging subject and the light-detecting portion for respective wavelengths.

By doing so, even if the light-receiving sensitivity of the light-detecting portion for each wavelength is different, by emitting illumination light beams from the respective light sources in a light-level balance in accordance with the light-receiving sensitivity, it is possible to detect the reflected light in an even more appropriate light-level balance.

In the above-described aspect, a light-level balance of the illumination light beams emitted from the respective light sources may be determined so as to be decreased with an increase in a value obtained for each wavelength by multiplying a transmittance of the reflected light between the imaging subject and the light-detecting portion with a light-receiving sensitivity of the light-detecting portion.

In the above-described aspect, the light-source portion and more than one of the light-detecting portions that detects the reflected light for each wavelength may be provided, the light-source portion may be provided with a plurality of light sources that emit a plurality of illumination light beams having different wavelengths, and a light-receiving area in each of the light-detecting portions for the reflected light for each wavelength may be determined so as to be decreased with an increase in a transmittance of the reflected light between the imaging subject and the light-detecting portion for each wavelength.

By doing so, even if the light levels of the illumination light beams emitted from the respective light sources of the light-source portion are set to be uniform, by employing the light-detecting portion in which the light-receiving area for each wavelength is determined so as to be decreased with an increase in the transmittance of the medium covering the imaging subject for each wavelength, it is possible to detect reflected light in an appropriate light-level balance, and thus, it is possible to perform observation by using an image having a high color reproducibility.

In the above-described aspect, the light-source portion and more than one of the light-detecting portion that detects the reflected light for each wavelength may be provided, the light-source portion may be provided with a plurality of light sources that emit a plurality of illumination light beams having different wavelengths, and a light-receiving area in each of the light-detecting portions for the reflected light for each wavelength may be determined so as to be decreased with an increase in a light-receiving sensitivity of the light-detecting portion for each wavelength.

In the above-described aspect, the light-source portion and more than one of the light-detecting portion that detects the reflected light for each wavelength may be provided, the light-source portion may be provided with a plurality of light sources that emit a plurality of illumination light beams having different wavelengths, and a light-receiving area in each of the light-detecting portions for the reflected light for each wavelength may be determined so as to be decreased with an increase in a value obtained for each wavelength by multiplying a transmittance of the reflected light between the imaging subject and the light-detecting portion with a light-receiving sensitivity of the light-detecting portion.

In the above-described aspect, the light-detecting portion may be provided with a band-pass filter that allows only light in a wavelength band of the reflected light to pass therethrough, and a detector that detects the light that has passed through the band-pass filter.

By doing so, by preventing light having a wavelength other than those in the wavelength band of the reflected light from being detected by the detector, it is possible to acquire an image having a high SN ratio.

In the above-described aspect, the light-detecting portion may be provided with a polarizing member that blocks the illumination light emitted from the illumination-light emitting portion and that allows reflected light coming from a scanning position in the imaging subject to pass therethrough.

By doing so, only the reflected light in which polarization thereof has been changed by being emitted from the illumination-light emitting portion and reflected at the scanning position in the imaging subject is detected by passing through the polarizing member, and, by preventing the illumination light emitted from the illumination-light emitting portion from directly being detected by the light-detecting portion, it is possible to acquire an image having a high SN ratio.

In the above-described aspect, at least one of the light sources may emit infrared or near-infrared illumination light.

By doing so, even in the case in which the medium covering the imaging subject is thick, it is possible to detect infrared light or near-infrared light in which the transmittance in the medium is high by using the light-detecting portion, and thus, it is possible to clearly observe the structure of the imaging subject.

In the above-described aspect, there may be provided with: a second endoscope system that is provided with the light-detecting portion and a transmitting portion that transmits a signal based on the reflected light detected by the light-detecting portion; the illumination-light emitting portion; a receiving portion that receives the signal transmitted by the transmitting portion; and an image-forming portion that generates an image on the basis of the signal received by the receiving portion.

By doing so, the intensity information of the reflected light coming from the imaging subject detected by the light-detecting portion is transmitted to the first endoscope system from the second endoscope system by means of the transmitting portion in the form of signals. The receiving portion of the first endoscope system receives the signals from the transmitting portion of the second endoscope system, the received signals are input to the image-forming portion, and thus, an image is generated. In other words, by wirelessly connecting the first and second endoscope systems, it is possible to further enhance the degree of freedom of manipulation without depending on the first endoscope system, or causing problems such as a cable becoming entangled or the like.

The present invention affords an advantage in that it is possible to decrease the invasiveness when being inserted into the body of a patient and to observe light that returns from an imaging subject and that has a wavelength that is substantially equivalent to that of illumination light.

REFERENCE SIGNS LIST 1, 22, 23 scanning endoscope system
2 inserted portion (illumination-light emitting portion)
3 light-source portion
4 light-detecting portion
5 image-acquisition portion
9 light-scanning portion
12a, 12b, 12c laser light source (light source)
14 avalanche photodiode (detector)
16 image-forming portion
18 band-pass filter
20 first polarizing member (polarizing member)
21 second polarizing member (polarizing member)
25 receiving portion
26 transmitting portion
A imaging subject

The invention claimed is:

1. A scanning endoscope system comprising:
   an insertion portion that is inserted into a body of a patient and configured to emit illumination light beams emitted from a plurality of light sources toward an imaging subject in the body in a spot-like manner, wherein the plurality of light sources emit a plurality of illumination light beams having different wavelengths;
   an actuator configured to scan the illumination light beams on the imaging subject;
   a light sensor disposed at a body surface of the patient, the light sensor being configured to detect reflected light beams coming from a scanning position in the imaging subject, at which the illumination light is scanned by the actuator;
   a controller configured to:
      determine light levels of the plurality of illumination light beams emitted from the plurality of light sources in accordance with transmittances of the reflected light beams between the imaging subject and the light sensor;
      determine a light-level balance of the illumination light beams emitted from the plurality of light sources with the transmittances of the reflected light beams, wherein the light levels of the plurality of illumination light beams decrease with an increase in the transmittances of the reflected light beams between the imaging subject and the light sensor for respective wavelengths; and
      control the plurality of light sources in accordance with the determined light-level balance of the illumination light beams emitted from the plurality of light sources.

2. A scanning endoscope system according to claim 1, wherein the light sensor detects reflected light beams having wavelength that is substantially equivalent to that of the illumination light beams.

3. A scanning endoscope system according to claim 2, wherein the controller determines a light-level balance of the illumination light beams emitted from the plurality of light sources so as to be decreased with an increase in light-receiving sensitivities between the imaging subject and the light sensor for respective wavelengths.

4. A scanning endoscope system according to claim 2, wherein the controller determines a light-level balance of the illumination light beams emitted from the plurality of light sources so as to be decreased with an increase in a value obtained for each wavelength by multiplying a transmittance of the reflected light beams between the imaging subject and the light sensor with a light-receiving sensitivity of the light sensor.

5. A scanning endoscope system according to claim 2, wherein at least one of the plurality of light sources emits infrared or near-infrared illumination light.

6. A scanning endoscope system according to claim 1, wherein the controller determines a light-level balance of the illumination light beams emitted from the plurality of light sources so as to be decreased with an increase in light-receiving sensitivities between the imaging subject and the light sensor for respective wavelengths.

7. A scanning endoscope system according to claim 1, wherein the controller determines a light-level balance of the illumination light beams emitted from the plurality of light sources so as to be decreased with an increase in a value obtained for each wavelength by multiplying a transmittance of the reflected light beams between the imaging subject and the light sensor with a light-receiving sensitivity of the light sensor.

8. A scanning endoscope system according to claim 1, wherein the light sensor is among more than one light sensors configured to detect the reflected light beams of respective wavelengths, and
a light-receiving area for the reflected light beams of respective wavelengths, for each of the more than one light sensors, is determined, wherein the light receiving area decreases with an increase in the transmittances of the reflected light beams between the imaging subject and the light sensor for each wavelength.

9. A scanning endoscope system according to claim 1, wherein the light sensor is among more than one light sensors configured to detect the reflected light beams of respective wavelengths, and
a light-receiving area for the reflected light beams of respective wavelengths, for each of the more than one light sensors, is determined, wherein the light receiving area decreases with an increase in a light-receiving sensitivity of the light sensor for each wavelength.

10. A scanning endoscope system according to claim 1, wherein the light sensor is among more than one light sensors configured to detect the reflected light beams of respective wavelengths, and
a light-receiving area for the reflected light beams of respective wavelengths, for each of the more than one light sensors, is determined, wherein the light receiving area decreases with an increase in a value obtained for each wavelength by multiplying a transmittance of the reflected light beams between the imaging subject and the light sensor with a light-receiving sensitivity of the light sensor.

11. A scanning endoscope system according to claim 1, wherein the light sensor is provided with a band-pass filter that allows light in a wavelength band of the reflected light beams to pass therethrough, and a sensor that detects the light that has passed through the band-pass filter.

12. A scanning endoscope system according to claim 1, wherein the light sensor is provided with a polarizing member that blocks the illumination light beams emitted from the insertion portion and that allows reflected light beams coming from a scanning position in the imaging subject to pass therethrough.

13. A scanning endoscope system according to claim 1, wherein at least one of the plurality of light sources emits infrared or near-infrared illumination light.

14. A scanning endoscope system according to claim 1, further comprising:
a second endoscope system that is provided with the light sensor and a transmitter that transmits a signal based on the reflected light beams detected by the light sensor;
the insertion portion;
a receiver that receives the signal transmitted by the transmitter; and
the controller, wherein the controller is configured to generate an image on the basis of the signal received by the receiver.

* * * * *

UNITED STATES PATENT AND TRADEMARK OFFICE
CERTIFICATE OF CORRECTION

PATENT NO. : 10,568,495 B2
APPLICATION NO. : 15/846537
DATED : February 25, 2020
INVENTOR(S) : Yamada et al.

It is certified that error appears in the above-identified patent and that said Letters Patent is hereby corrected as shown below:

On the Title Page

(30) Foreign Application Priority Data should read:
Jun. 24, 2015 (JP)..................PCT/JP2015/068195
Mar. 4, 2016 (JP)............................2016-042461

Signed and Sealed this
Fifth Day of May, 2020

Andrei Iancu
*Director of the United States Patent and Trademark Office*